(12) United States Patent
Farmer

(10) Patent No.: US 11,796,835 B2
(45) Date of Patent: Oct. 24, 2023

(54) INTERCHANGEABLE EYEWEAR SYSTEM

(71) Applicant: Andrew Farmer, Encinitas, CA (US)

(72) Inventor: Andrew Farmer, Encinitas, CA (US)

(*) Notice: Subject to any disclaimer, the term of this patent is extended or adjusted under 35 U.S.C. 154(b) by 310 days.

(21) Appl. No.: 16/757,014

(22) PCT Filed: Oct. 15, 2018

(86) PCT No.: PCT/US2018/055912
§ 371 (c)(1),
(2) Date: Apr. 17, 2020

(87) PCT Pub. No.: WO2019/079196
PCT Pub. Date: Apr. 25, 2019

(65) Prior Publication Data
US 2020/0271952 A1    Aug. 27, 2020

(51) Int. Cl.
*G02C 5/14*    (2006.01)
(52) U.S. Cl.
CPC ......... *G02C 5/146* (2013.01); *G02C 2200/08* (2013.01)

(58) Field of Classification Search
CPC ............... G02C 5/146; G02C 2200/08; G02C 2200/04; G02C 2200/26; G02C 9/00; G02C 1/10; G02C 1/04; G02C 1/06; A61F 9/025
USPC .......................................... 351/41, 111, 116
See application file for complete search history.

(56) References Cited

U.S. PATENT DOCUMENTS

| 4,822,158 A * | 4/1989 | Porsche .................. G02C 1/04 351/124 |
| 6,450,637 B1 * | 9/2002 | Zelman .................... G02C 1/04 351/57 |
| 2017/0100287 A1 * | 4/2017 | Calilung ................ G02C 11/08 |

* cited by examiner

*Primary Examiner* — Tuyen Tra
(74) *Attorney, Agent, or Firm* — John R. Ross; John R. Ross, III

(57) ABSTRACT

An eyewear device having a frame positionable to a removable engagement with any of a plurality of lens assemblies. Each lens assembly has shoulders at opposing ends which slidably engage within respective shoulder slots formed into the body of the frame. A biased ball having a portion extending into one or both shoulder slots, biasly contacts into a ball cavity depending into a respective shoulder to maintain the lens assembly in the removable engagement.

18 Claims, 8 Drawing Sheets

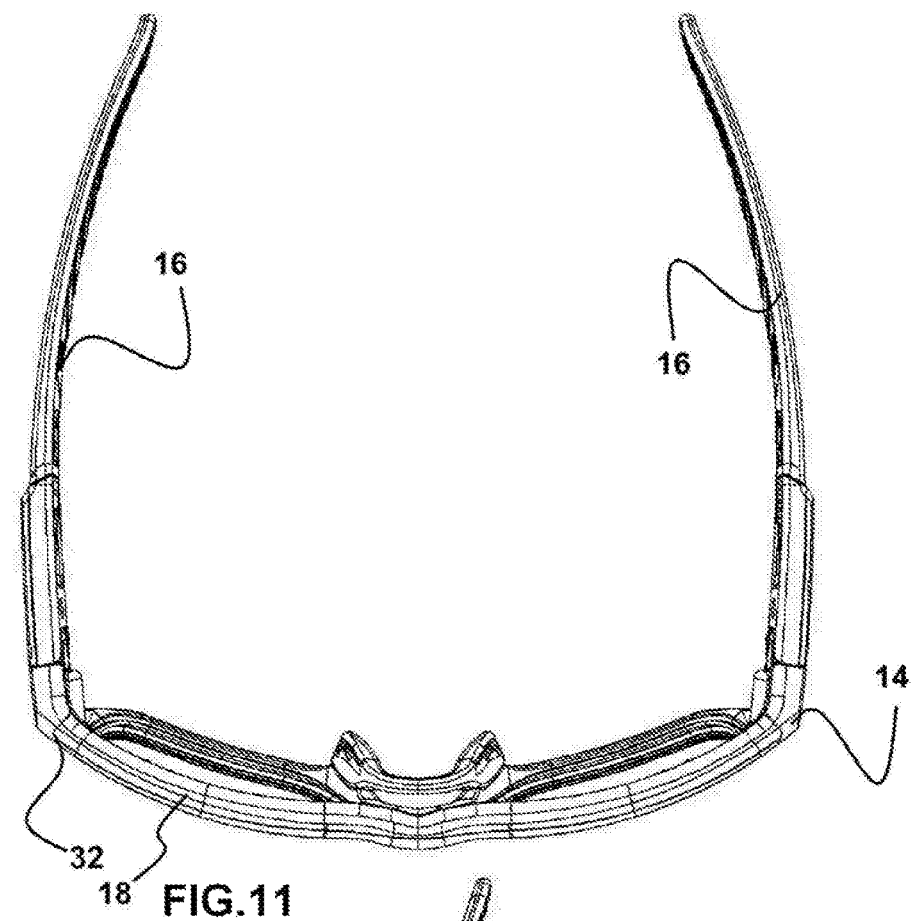
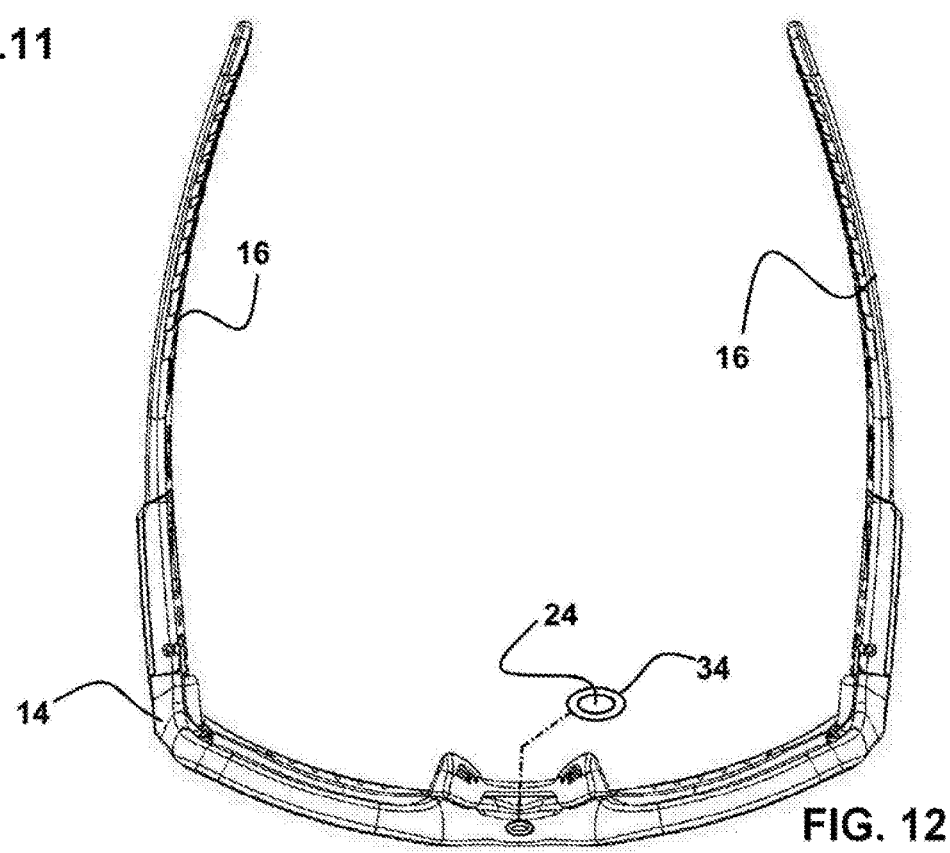

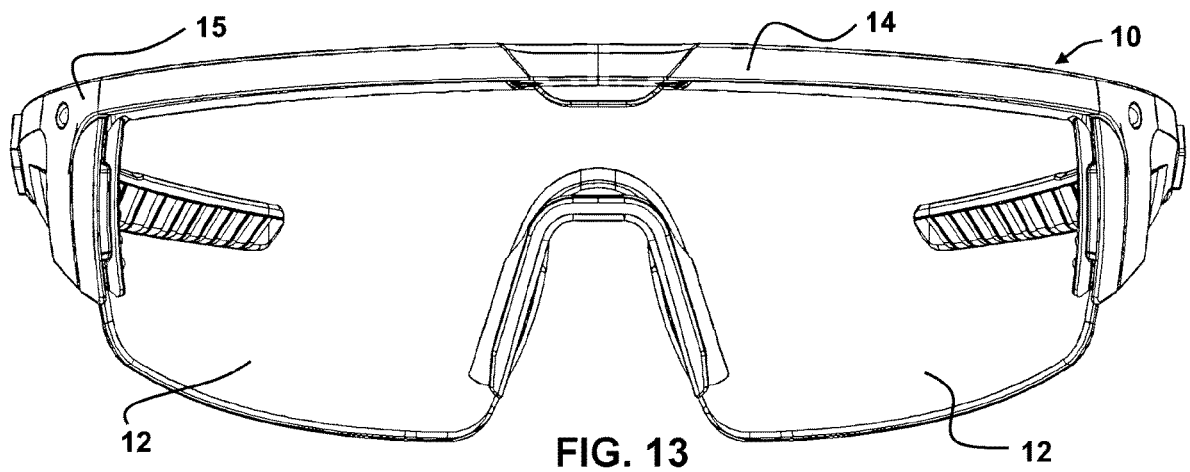
FIG. 13
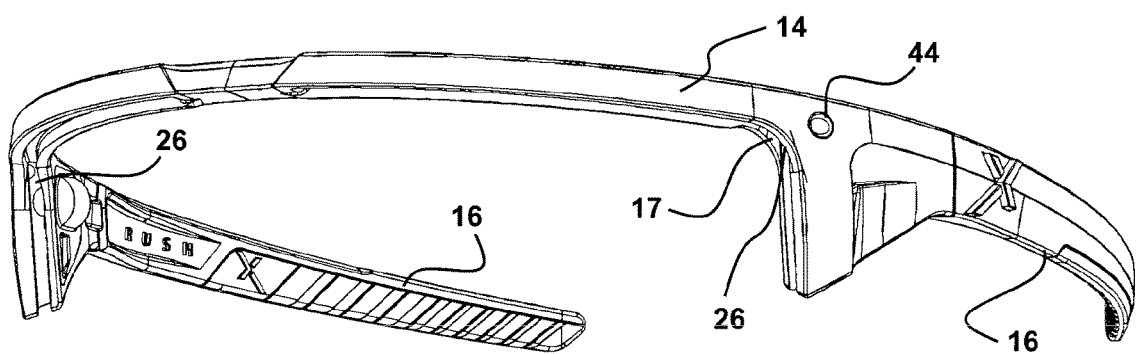
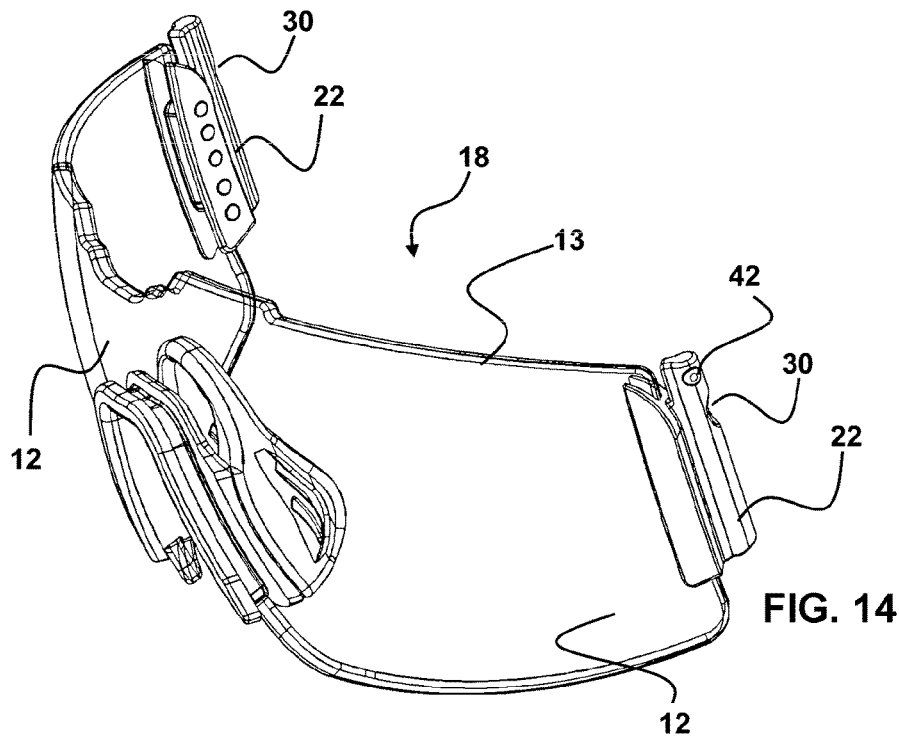
FIG. 14

INTERCHANGEABLE EYEWEAR SYSTEM

This application claims priority to U.S. Provisional Patent Application Ser. No. 62/574,653 filed on Oct. 19, 2017, and also to U.S. Provisional Patent Application Ser. No. 62/730,135 filed on Sep. 12, 2018, which are included herein in their respective entirety by this reference thereto.

BACKGROUND OF THE INVENTION

1. Field of the Invention

The present invention relates generally to eyewear.

More particularly, it relates to eyewear employing an eyeglass frame which is configured for user engagement of one or a plurality of paired lenses thereby allowing users to adapt their eyeglass lenses to the purpose or venue where they will be worn.

2. Prior Art

Eyeglasses conventionally employ an eyeglass frame adapted for positioning in front of the eyes of the user, which has temples which extend to the tops of the ears of the user. The frame is positioned with a bridge portion atop the nose of the user, whereupon the extending temples engaged with the ears maintain the plane of the lenses in proper position for viewing therethrough by the eyes of the user.

Conventionally, each pair of lenses worn by a user, is permanently engaged with the eyeglass frame with which it was provided. As a consequence, users wearing corrective lenses may have multiple pairs of eyeglasses, with each in a different frame, to provide them with different types of lenses depending on the intended use and the venue and the time of day.

For outdoor use during the day, a user may have a pair of tinted or polarized lenses to protect their eyes from sunlight and to make outdoor viewing more comfortable in bright light. However, for some users, the color and light-blocking ability of such lenses can vary during a given day. For example, in bright sunlight, a darker lens which tints or blocks more sunlight may be required. However, later in the day or at dusk, the lenses, which were comfortable in bright sunlight, may obscure the view of the user at dusk and in low light.

In the evening or indoors, the tinted or polarized lenses which work outdoors, are not well adapted for use. Consequently, users with corrective lenses might have yet a third eyeglass frame hosting a third pair of eyeglasses for evening use or in venues where tinted lenses might shadow their vision.

While some users may not mind the cost and inconvenience of having to store, transport, and use multiple pairs of eyeglasses mounted in multiple frames, it is at best an inconvenient and troublesome way to provide proper vision in differing circumstances. However, where the eyeglass frames are custom, or expensive designer frames, having and employing multiple different and expensive frames to have eyeglasses suitable for differing light conditions and venues, becomes cost prohibitive.

The system herein provides a single eyeglass frame which is configured for the easy and quick engagement and removal of any pair of eyeglass lenses or shields, from a kit including one or a plurality of pairs of lenses or shields. The system is especially well adapted to allow users having inexpensive frames, or very expensive designer frames, or custom fit frames, to employ a single eyeglass frame of choice, into which they can choose to engage any of the multiple pairs of lenses or shields provided in a kit of lenses, as needed.

It should be noted, the foregoing examples of related art for eyeglass frames and lenses and the like and limitations related therewith are intended to be illustrative and not exclusive, and they do not imply any limitations on the eyeglass frame system described and claimed herein. Various limitations of the related art are already known or will become apparent to those skilled in the art upon a reading and understanding of the specification below and the accompanying drawings.

An object of the present invention is the provision of an individual eyeglass frame which is configured for the engagement by a user, of any shield or pair of lenses from a plurality of such pairs of lenses which are configured for differing light circumstances, correction, safety, fashion and venues.

Another object of the present invention is to provide such an eyeglass frame system which will allow users to reduce costs through the employment of a single eyeglass frame, to which they can choose to engage any of a plurality of different corrective and light filtering lenses.

Further objectives of the eyeglass frame system herein will be brought out in the following parts of the specification wherein the summary and detailed description of the invention are for the purpose of fully disclosing the invention without placing limitations thereon.

SUMMARY OF THE INVENTION

The present invention provides a device and method solving the shortcomings and dilemma in the prior art of eyeglass frames which currently require users to own multiple eyeglass frames where a user desires to use multiple shields or pairs of lenses for differing conditions and purposes.

The disclosed device herein in a number of modes shown, provides an eyeglass frame which is configured for the easy engagement, disengagement, and re-engagement of a plurality of pairs of eyeglass lenses or frames forming dual lenses. The system allows users to have a single eyeglass frame, which might be an expensive designer frame or a custom built frame for their individual facial structure, and to then engage any pair of lenses from a kit including a plurality of different lens pairs each of which fits into the frame easily and quickly.

The eyeglass frame features individual openings sized for operative engagement along at least one perimeter edge of lenses engaged thereto. In operative engagement, with the frame in an as-used position in front of the eyes of the user, each opening holding a respective lens or lens portion, will substantially align the center of the lens with the pupil of the eye of the user during subsequent use.

Each lens opening in the lens frame body, communicates with a substantially U-shaped recess or race depending into all or a portion the perimeter surface and running around the perimeter edge of the lens opening in the frame. The race is shaped and sized to operatively engage with a portion of the perimeter edge of a respective lens which may be inserted into the race and removed therefrom. Insertion and removal of the lenses in their engagement with an insert body is accomplished through an opening formed at a top or bottom edge of the frame.

The lenses are engaged with a connecting member on one or both sides and configured to frictionally engage on opposing edges of the lenses with the race or recess of the frame. Thus, a lens inserted into the opening of the eyeglass frame is operatively engaged about substantially an entire perimeter edge of each lens. Shoulders engaged to opposing sides of the lens or the connecting member, are positioned to operatively engage within respective slots formed in the eyeglass frame to provide a secure mount therewith.

In a particularly preferred mode of the device, a biased ball located on opposing sides of the eyeglass frame is continuously biased to position a portion of each respective biased ball within one slot where the ball will engage within a recess formed in the respective shoulder inserted into the slot under a biased force. This biased engagement of a ball within each recess of each shoulder portion is preferred because it maintains the lenses in a solid engagement with the frame. This solid biased engagement is important where the assembled eyewear is subjected to jostling in a purse or container or other sharp movements to prevent a dismount of lenses and connecting member from the frame.

Also provided, in one mode, is a projecting center post extending from a central portion of the connecting member between both lenses. This center post operatively engages within a central cavity formed in the lens frame. An opening, communicating with the nose bride of the frame forms a viewing window where the proper positioning of the projecting post into the central cavity defines an indicator showing proper engagement of the lenses and connecting member with the eyeglass frame.

The lenses are preferably provided as a kit of lenses where each shield forming a pair of lenses or each pair of lenses in the kit, has a differing optical quality or lens configuration. For example, optical quality can include darkness of tint, color of tint, optical correction, polarization, metallic reflective surfaces, color and other optical quality. Differing lens configuration could include, for example, plastic lenses, glass lenses, safety lenses, laser or flash safety lenses, and other structural and safety configurations.

In use, a user can change the lenses positioned in any lens opening in any frame, by removing the connecting member and both lenses from their engagement with the eyeglass frame. Any lens pair engaged with a connecting member may be chosen and thereupon engaged with the eyeglass frame by engaging the lens perimeter edge with a race or recess depending into the body of the frame and engaging the shoulders with the proper mating slot depending into the body of the frame. Once so engaged, the ball communicating into each slot, will removably position to a biased engagement within a respective recess depending into the shoulders. Easy removal and reengagement is accomplished by pulling on a central area of the connecting member to thereby overcome the frictional engagement of the shoulders with the slots depending into the body of the eyeglass frame, and if present, the biased contact of the ball with the recess formed in each shoulder.

With respect to the above description, before explaining at least one preferred embodiment of the herein disclosed user configurable eyeglass frames in detail, it is to be understood that the invention is not limited in its application to the details of construction and to the arrangement in the following description or illustrated in the drawings. The disclosed eyewear frame and system herein described is capable of other embodiments and of being practiced and carried out in various ways which will become obvious to those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based, may readily be utilized as a basis for the designing of other eyeglass frames which are configured to engage multiple pairs of lenses and for carrying out the several purposes of the present disclosed device. It is important, therefore, that the claims herein be regarded as including such equivalent construction and methodology, insofar as they do not depart from the spirit and scope of the present invention.

BRIEF DESCRIPTION OF DRAWING FIGURES

The accompanying drawings, which are incorporated herein and form a part of the specification, illustrate some, but not the only or exclusive examples of embodiments and/or features of the leash invention. It is intended that the embodiments and figures disclosed herein are to be considered illustrative rather than limiting.

Figure 4:
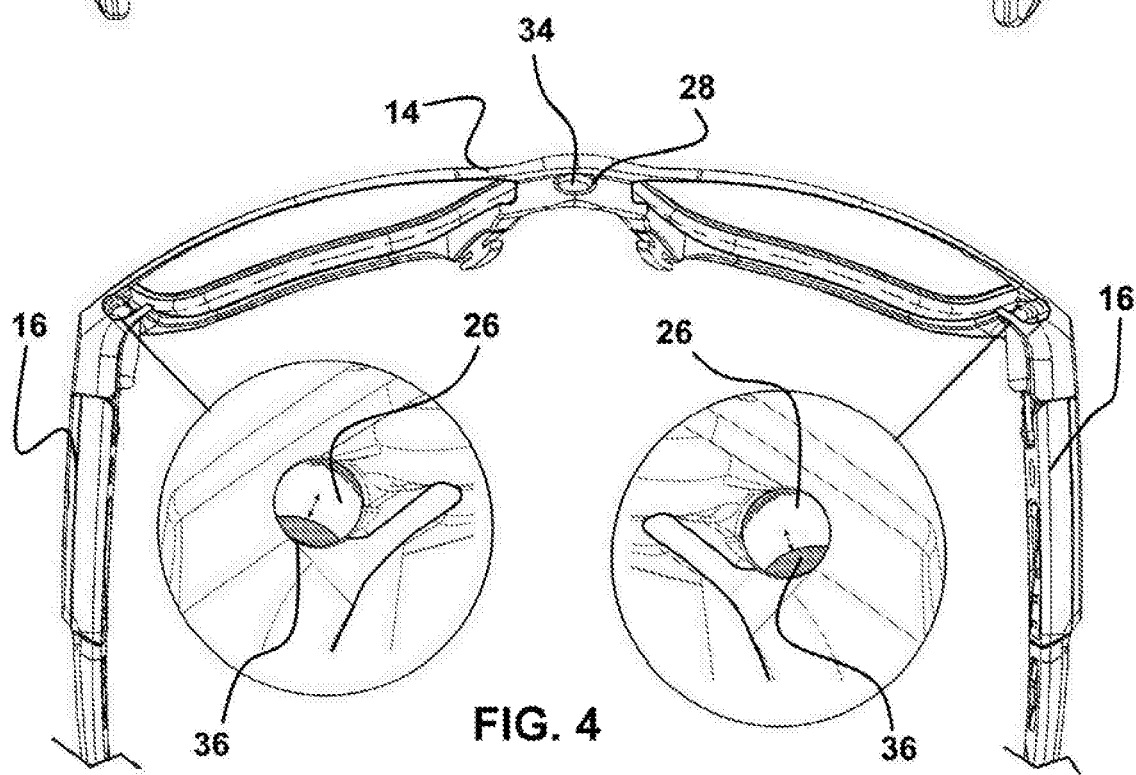

FIG. 4 shows bottom perspective view of an eyeglass frame of the eyewear herein, ready for insertion of the lens assembly, and showing an opening or window communicating with the post slot in the nose bridge, and showing enlarged views of a biased ball slidably positioned in the frame biased to project into one or both of two shaped shoulder slots which depend into opposite sides of the body of the frame.

Figure 5:
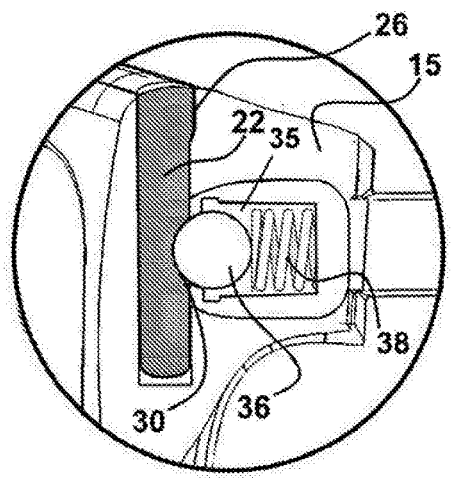

FIG. 5 depicts the biased ball assembly which is preferred for inclusion herein to provide a biased contact of the ball into and with the ball recess depending into a side surface of each shoulder extending from the assembly, each of which is positioned to engage with a ball once the shoulder is fully inserted into a respective shoulder slot formed on opposing sides of the frame.

Figure 1:
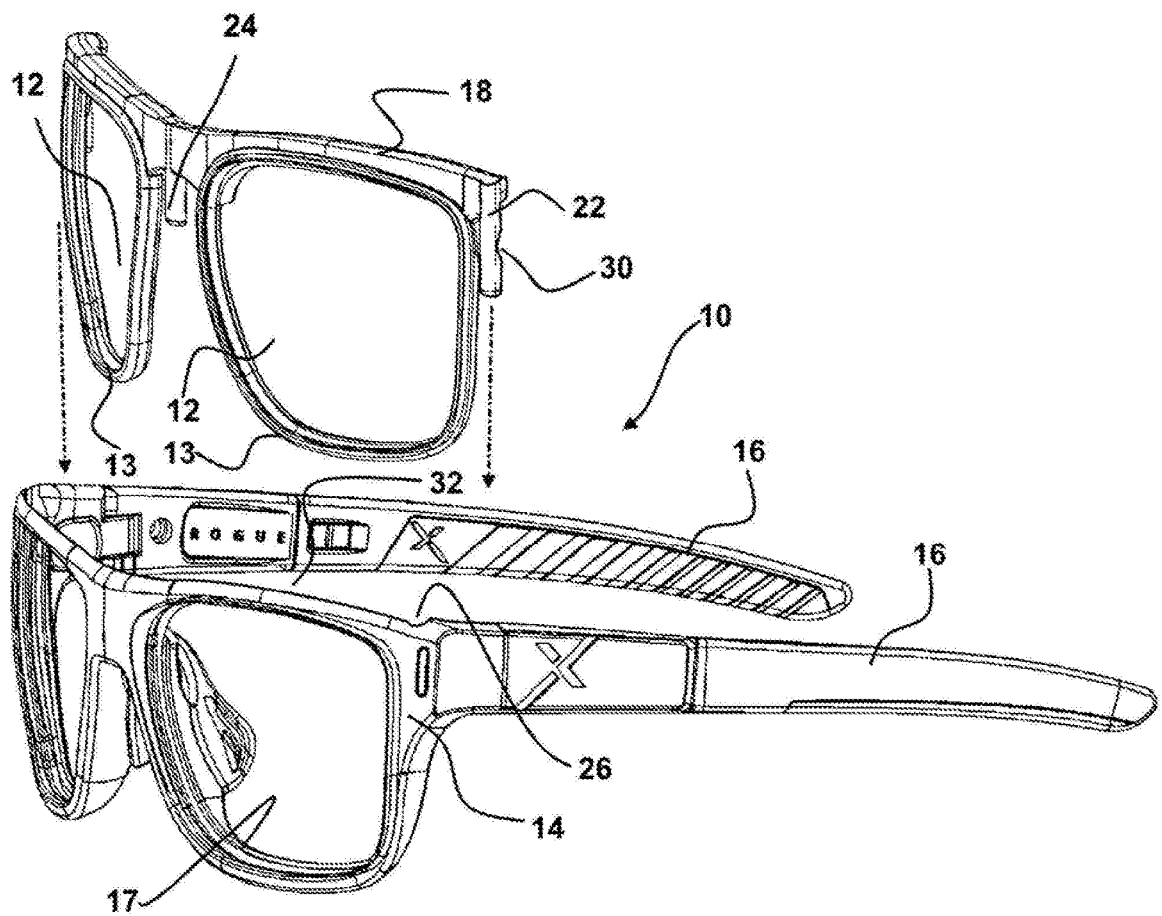
FIG. 1 shows an exploded view of an eyeglass frame herein with a lens assembly formed of two lenses extending from a connecting member positioned for an insertion within a mating opening formed in the body of the frame, and showing temples extending from the body of the frame.
Figure 6:
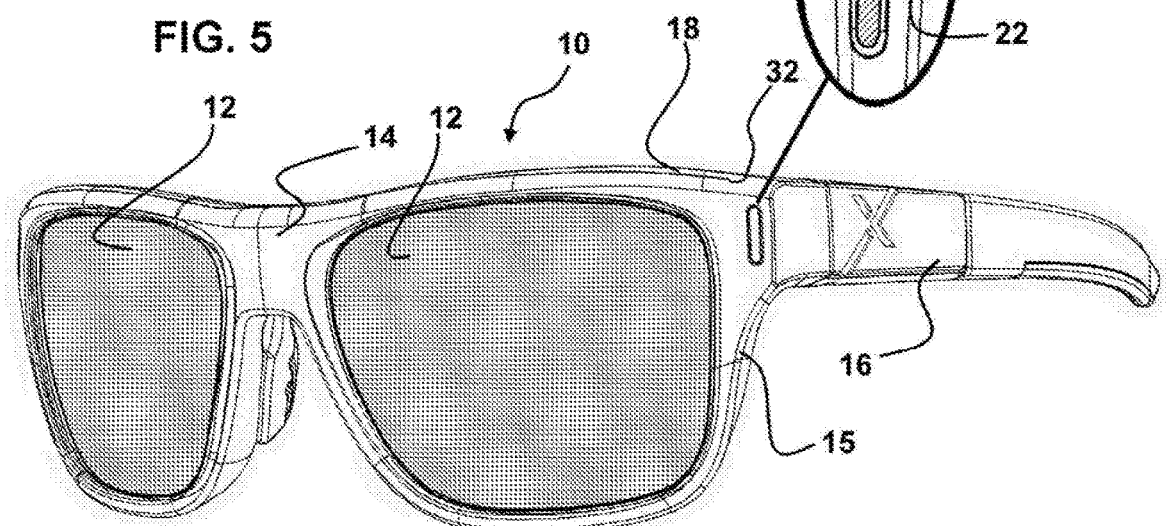

FIG. 6 shows the device as in FIG. 1, with the lens assembly operatively engaged with the frame and shows an optional view slot or window in the body of the frame allowing viewing of the shoulders to ascertain proper engagement in a respective shoulder slot.

Figure 2:
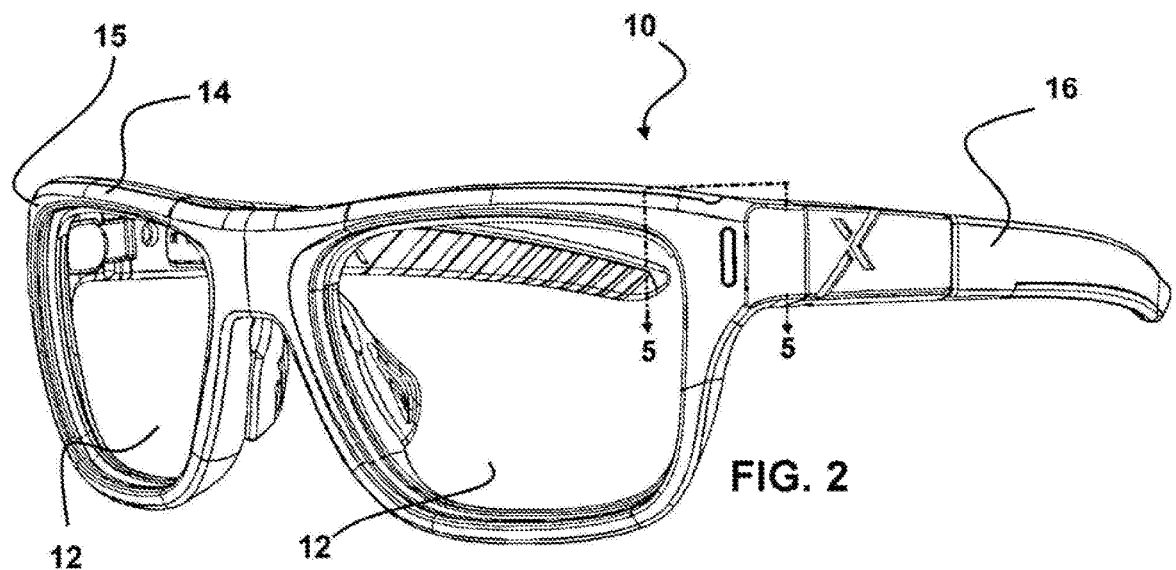
FIG. 2 shows the device of FIG. 1, in an assembled configuration with the lens assembly operatively engaged with the eyeglass frame.
Figure 7:
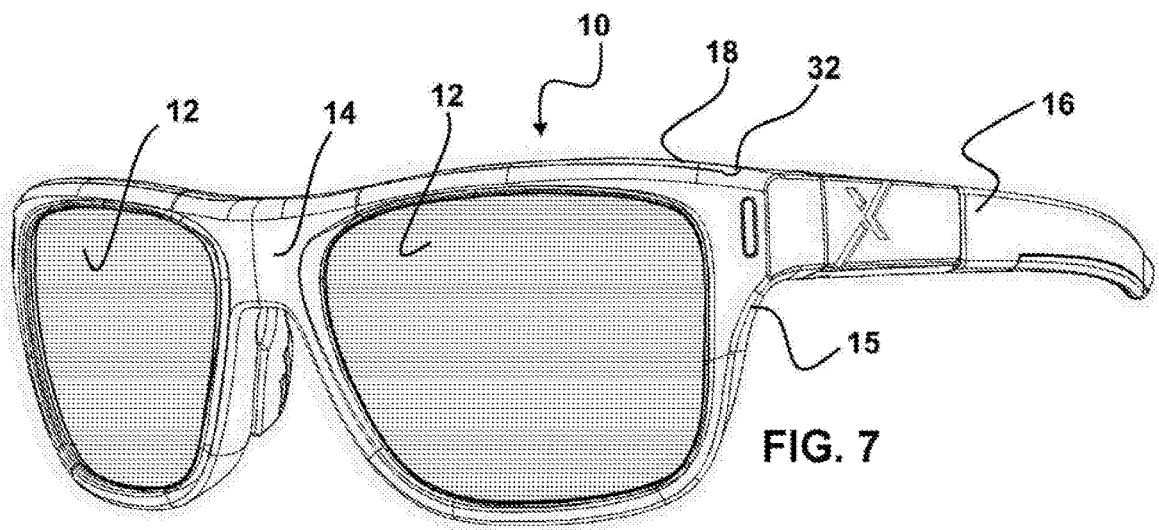

FIG. 7 depicts the device as in FIG. 1 and similar to that of FIG. 6, where is depicted lenses having different shading characteristics from the clear lenses of FIGS. 1-2 and the tinted lens of FIG. 6, thereby showing the utility of the device to allow lens changes of differing lens assemblies from a plurality, to accommodate different uses and venues.

Figure 8:
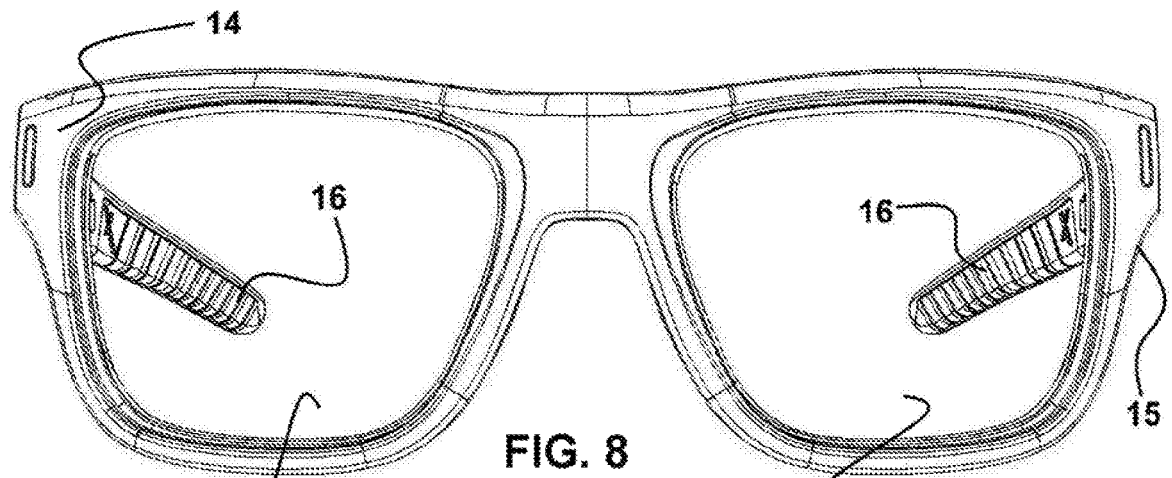

FIG. 8 is a front side view of the device of FIG. 2.

Figure 9:
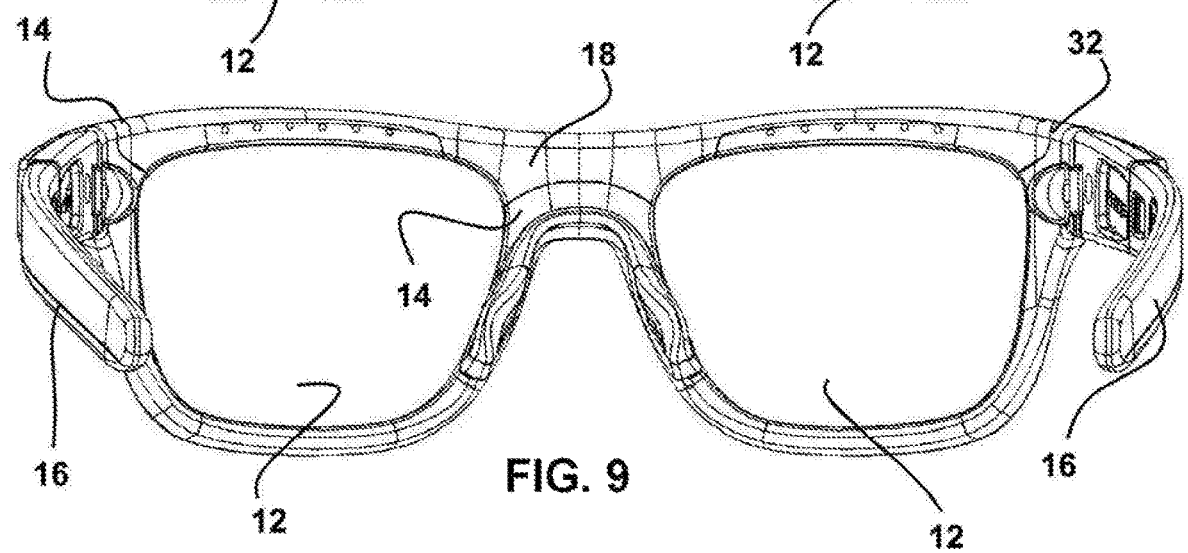

FIG. 9 is a rear side view of the device of FIG. 2.

Figure 10:
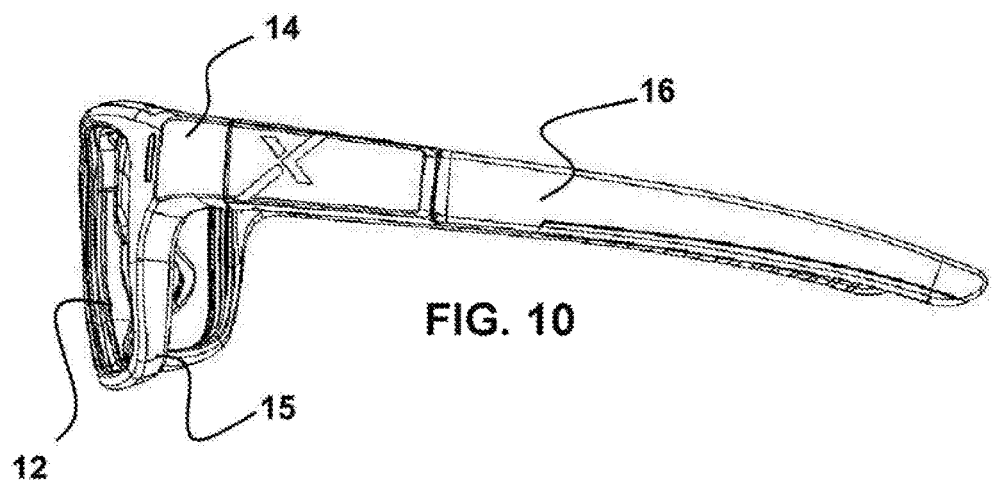

FIG. 10 is one side view of the device of FIG. 2 with the opposite side view being a mirror image thereof.

FIG. 11 is a top side view of the device of FIG. 2.

FIG. 12 is a bottom view of the device of FIG. 2 opposite the view of FIG. 11 also showing an enlarged viewing window communicating with the bridge area of the eyeglass frame.

FIGS. 13-14 shows a mode of the device herein wherein the lens assembly lenses are formed as a shield and the two opposing shoulders extend from opposite sides of the shield.

Figure 15:
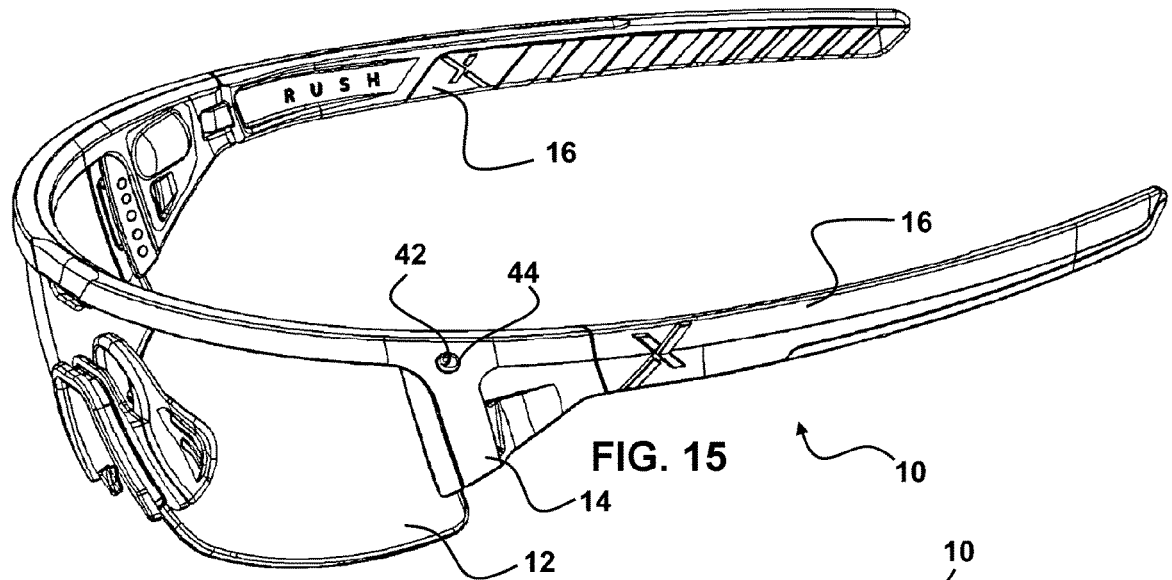

FIG. 15 depicts the device herein, as in FIG. 13, assembled from the components of FIG. 14, showing a perspective side view thereof.

Figure 16:
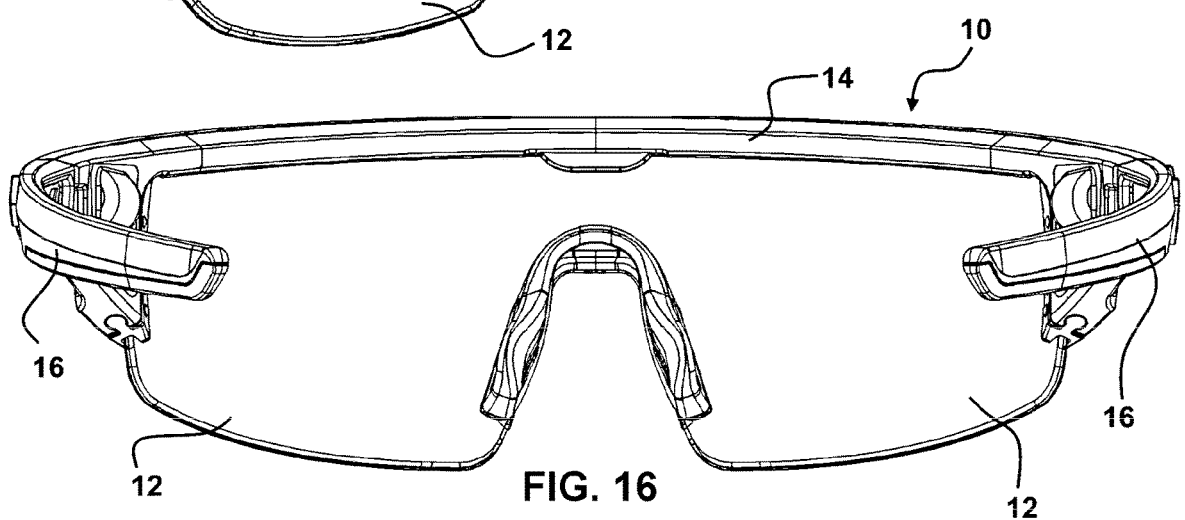

FIG. 16 shows a rear side view of the device of FIG. 13.

Figure 17:
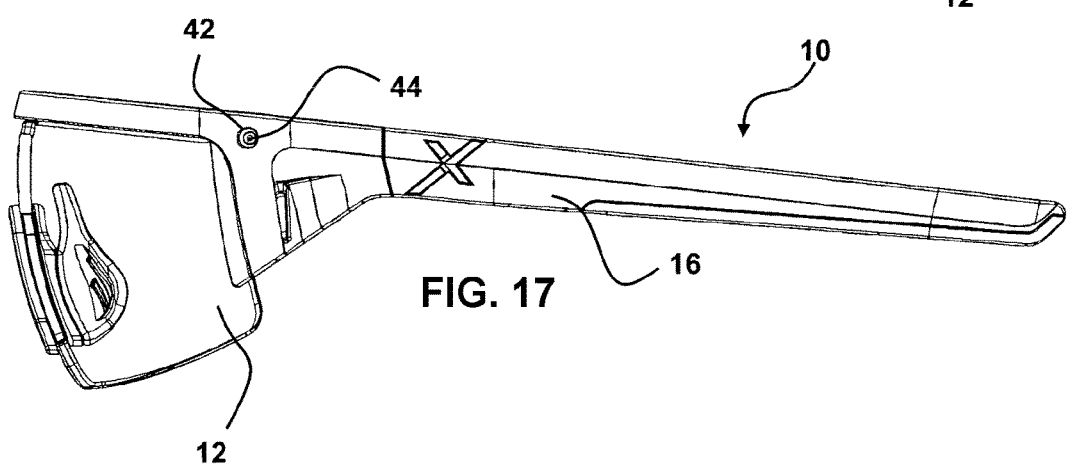

FIG. 17 shows one side view of the device of FIG. 13 with the opposite side view being a mirror image thereof.

Figure 18:
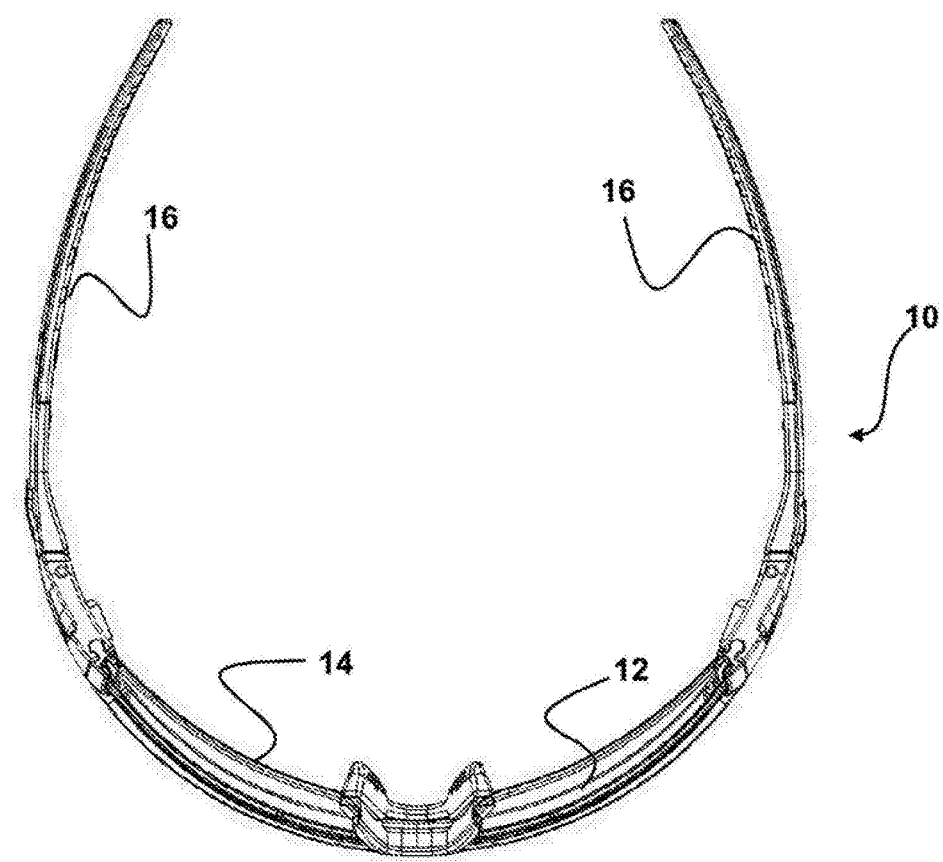

FIG. 18 depicts a bottom side view of the device of FIG. 13.

Figure 19:
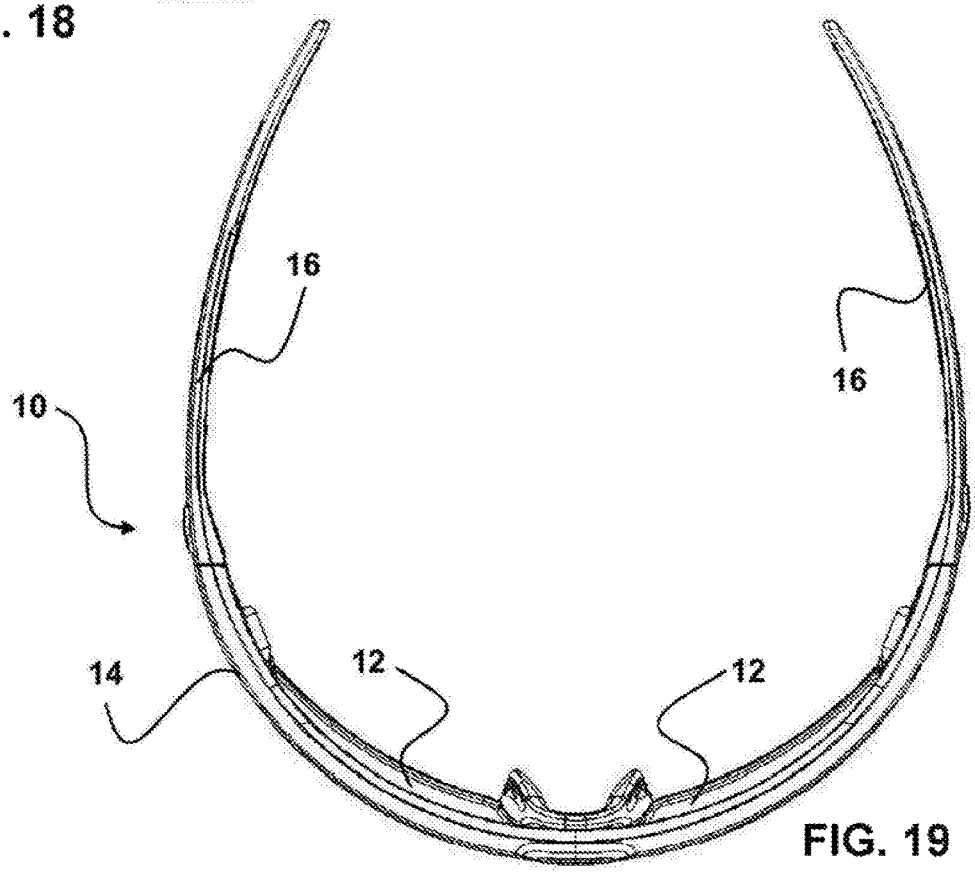

FIG. 19 shows a top side view of the device of FIG. 13.

DETAILED DESCRIPTION OF THE PREFERRED EMBODIMENTS OF THE INVENTION

In this description, any directional prepositions if employed, such as up, upwardly, down, downwardly, front, back, first, second, top, upper, bottom, lower, left, right and other such terms referring to the device or depictions as such may be oriented, are describing it such as it appears in the drawings and are used for convenience only. Such terms of direction and location are not intended to be limiting or to imply that the device herein has to be used or positioned in any particular orientation.

Now referring to drawing of FIGS. 1-19, there is seen in FIG. 1, the fully assembled modular eyewear device 10 configured to allow unlimited changes of the optical characteristics of the lenses 12 which are removably engaged with the frame 14 herein. Two temples 16 are shown rotationally engaged at first ends to opposing sides of the frame 14.

Also shown in FIG. 1 is the removably engageable lens assembly 18 each of which is formed of lenses 12 which are engaged on respective first sides with a connecting member 20. Shown projecting from opposing engagements either to the connecting member 20 or to opposite ends of the lenses 12, are first and second shoulders 22. In the mode of the device of FIG. 1, the lens assembly 18 may also include a centrally located post 24 which aids in engaging the lens assembly 18.

The first and second shoulders 22 as noted herein are positioned on opposing ends of the lens assembly 18 and engaged either to the lens 12 or to the connecting member 20. These shoulders 22 are especially preferred to form a secure engagement and an engagement registered in position relative to the frame 14. During engagement of the lens assembly 18 the first and second shoulders 22 align with and removably engage into shoulder slots 26, each of which depends into a respective opposing side of the frame 14.

While a tight frictional engagement can be achieved by forming the shoulders 22 of compressible material, or in a dimension equal to or just slightly smaller than the dimensions of the shoulder slots 26 in experimentation such made the lens assembly 18 frustrating to engage and disengage. To that end, forming the shoulders 22 in dimensions to easily slide into and out of respective shoulder slots 26 worked better and the potential for the lens assembly 18 dismounting unexpectedly is cured by a biased engagement of a translating ball 36 into ball recesses 30 which are formed in the shoulders 22. When included, the post 24 is removably engageable within a post slot 28 formed into the body of the frame 14 at a central portion thereof.

In use, the entire assembled lens assembly 18 is engageable with the body of the frame 14 through an opening 32 extending to a first side edge of the body 15 of the frame 14.

In a preferred mode of the eyewear device 10, to provide especially secure positioning, and maintain such during use such as when moving and during wind or air impacting against the lenses 12, the distal or leading edges 13 of each lens 12 are positioned to engage against a second side edge of the frame 14 securely, preferably such as depending into a lens slot 17. This lens slot 17 depends into the body 15 of the frame 14 along the second side edge opposite and facing the first side edge and is aligned with the opening 32 extending to the first side edge of the body 15 of the frame 14 at the opposite side thereof.

Shown in FIG. 2 is the device 10 of FIG. 1, in an assembled configuration with the lens assembly 18 operatively engaged with the body 15 of the eyeglass frame 14. Line 5-5 indicates a sectional view is found in FIG. 5 of the first and second shoulders 22 with respective shoulder slots 26. The device 10, in this assembled mode, is ready for use but, as noted, may be configured with any lens assembly 18 having any prescription and/or polarized and/or tinted lenses 12. Such lens assemblies 18 may be provided in a kit having a plurality of such lens assemblies 18 where each lens assembly 18 has a lens or lenses 12 with differing optical characteristics as to vision correction and/or tint and/or polarization or coatings or the like.

Figure 3:
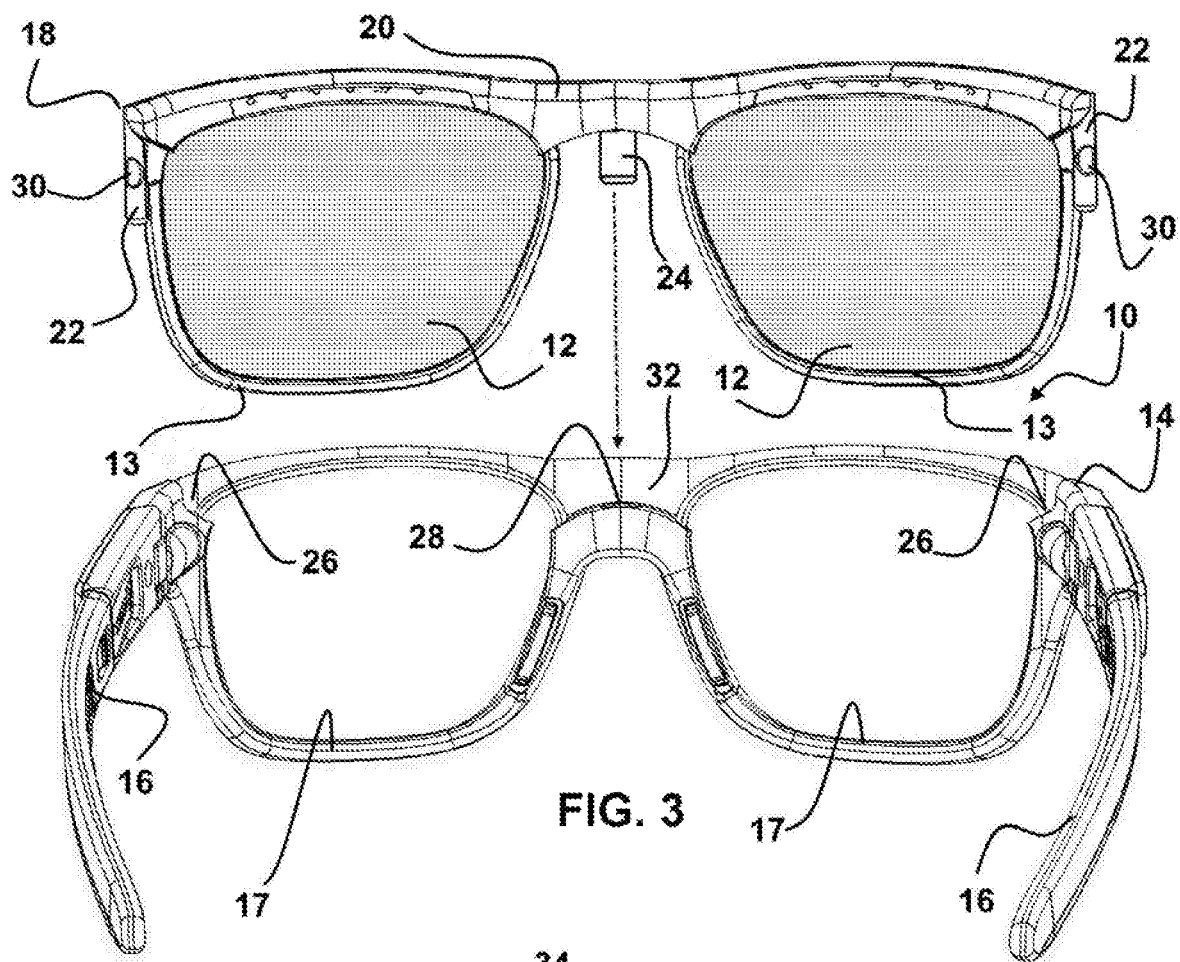
FIG. 3 depicts a rear view of the device herein of FIG. 1, showing the lens assembly positioned for insertion into an opening in the frame and showing a center post and two shoulders on opposing sides of the connecting member.

Shown in FIG. 3 is a rear side view of the device 10 herein in the exploded view of FIG. 1. As can be seen, a lens assembly 18 which may be chosen from a kit including a plurality of lens assemblies 18, is positioned for removable engagement with the frame 14. As shown such engagement is accomplished by insertion of the lens assembly 18 into the opening 32 depending inward from one side edge of the body 15 of the frame 14. Also shown, is the optional but preferred for stability and strength center post 24, and on opposing ends of the assembly 18, first and second shoulders 22. As noted, the first and second shoulders 22 are positioned on opposing sides of the two lenses 12 of the assembly 18, and may be engaged to the lenses 12 such as in FIG. 14, or as depicted in FIG. 1, with opposite sides of the connecting member 20. As noted, the lens assembly 18 so configured, positions first and second shoulders 22 in aligned positions to be slid within first and second shoulder slots 26, and if included, positions the post 24 for an insertion within the post slot 28 depending into a central portion of the body 15 of the frame 14, above the nose bridge.

In FIG. 4 is depicted a bottom perspective view of the eyeglass frame 14 ready for insertion of a chosen lens assembly 18 such as that of FIG. 3. Also shown on the bridge of the frame 14, is a window aperture 34 which communicates with the centrally positioned post slot 28 which has an interior dimension which is complimentary in shape to exterior surface defining the size and shape of the central post 24 extending from the central area of the connecting member 20. When provided, a view of the post 24 through the window aperture 34 allows the user to confirm proper engagement of the post 24 within the post slot 28, and thus the lens assembly 18 engagement with the body 15 of the frame 14. The leading edge of the post 24 may be colorized to allow the user to confirm the leading edge has contacted with the body 15 of the frame 14 at the terminating end of the post slot 28. In this fashion the user can confirm full engagement of the lens assembly 18 into the opening 32 in the body 15 of the frame 14.

Also shown in FIG. 4, are enlarged views of a translatable biased ball 36 which has a portion thereof biased into a position within a respective ball recess 30 formed into each shoulder slot 26. As noted, this ball 36 engagement is most preferred to provide ease of engagement and disengagement of the lens assembly 18 with the frame 14, by allowing the shoulders 22 to be dimensioned slightly smaller than the shoulder slots 26 and thereby to slide easily into and out of the respective shoulder slots 26. The ball 36 is slideable or translatable within a ball cavity 35 positioned in the body 15 of the frame 14.

A portion of each ball 36 under a biased force will translate in the ball cavity 35 in a direction away from the spring 38 or other biasing component, and will project into a respective shoulder slot 26. The portion of the ball 36 biased toward and projecting into the shoulder slot 26 will engage within a respective ball recess 30 formed into the side surface of a respective one of the first and second shoulders 22. While one ball 36 engaging against one ball recess 30 in one of the shoulders 22 will provide a biased connection to hold the lens assembly 18 engaged, two such balls 36 each engaging into a respective ball recess 30 in a respective one of the shoulders 22 is preferred as such provides a more secure engagement.

This biased positioning of a translating but biased ball 36 into each ball recess 30, as noted, prevents the lens assembly 18 from unintended disengagement due to sharp movements and the like. This biased but translating ball engagement thus provides a secure engagement which is easily disengaged by the user pulling upon the connecting member 20 and lens assembly 18, which causes the ball 36 to slide up the curved surface defining the ball recess 30 like a ramp, and overcoming the spring or other biasing force. Thus, a simple pulling of the lens assembly 18 away from the frame 14 will disengage the ball or balls 36, and disengage the shoulders 22 from the shoulder slots 26, thereby disengaging the lens assembly 18 from the frame 14. Engaging the same or a different lens assembly 18 from the plurality available to the user, is accomplished in reverse by pushing the lens assembly 18 toward the frame 14 with the shoulders 22 engaged with respective shoulder slots 26 wherein the balls 36 will be translated out of the shoulder slot 26 until a respective curved recess 30 aligns with a respective ball 36 which biasly engages therein.

As noted, FIG. 5 is a sectional view along line 5-5 of FIG. 2 and depicts the ball 36 in a biased engagement within the curved ramp of the ball recess 30 of each of the first and second shoulders 22 which slidably engage within a respective shoulder slot 26 formed into the body 15 of the frame 14. As noted, this biased engagement such as provided by the force of a biasing component such as a spring 38 maintains the lens assembly 18 in operative engagement with the frame 14. This engagement is maintained until the user exerts sufficient force to the lens assembly 18 to overcome the biasing force against the balls 36 whereupon the balls 36 slide against the surface of the ball recess 30 and retract out of the recess 30 during such removal.

In FIG. 6 is shown the device 10 as in FIG. 2, with the lens assembly 18 operatively engaged with the frame 14 and shows an optional window opening 40 communicating through the body 15 of the frame 14 into a shoulder slot 26. When provided, this window opening 40 provides a means to ascertain proper engagement of the lens assembly 18 into the formed opening 32 in one side of the body 15 of the frame 14 to thereby ascertain the shoulders 22 are in full and proper engagement in a respective shoulder slot 26. The lenses 12 shown in FIG. 6 are tinted.

Depicted in FIG. 7, the assembled device as in FIG. 2 is shown which is similar to that of FIG. 6. As shown, the depicted lenses 12 have different shading characteristics from the clear lenses of FIGS. 1-2 and the tinted lens 12 of FIG. 6 all of which may be included in a plurality of lens assemblies 18 of a user. This depicts the enhanced utility provided by the device 10 which is configured to allow any lens assembly 18 having any tinted, or corrective, or shaded, or reflective, or other lens 12 engaged therein, and thereby allow optical lens 12 characteristic changes to accommodate different uses and venues.

Shown in FIG. 8 is a front side view of the device of FIG. 2 which is the opposite of the rear side view shown in FIG. 9. FIG. 10 depicts one side view of the device 10 of FIG. 2 and the opposite side view is a mirror image thereof.

FIG. 11 shows a top side view of the eyewear device 10 assembled as in FIG. 2 showing the temples 16 rotated to open positions from rotational engagements with the frame 14. An opposite bottom view of the device of FIG. 2 is shown in FIG. 12, which also depicts an enlarged window aperture 34 communicating with the bridge area of the eyeglass frame through which a properly engaged post 24 can be viewed to confirm proper engagement of the lens assembly 18 into the frame 14.

Depicted in FIGS. 13-14 are another mode of the user configurable eyewear device 10 which is adapted to allow engagement of any of a plurality of single lens 12 lens assemblies 18 into a removable engagement with a frame 14. As shown, the shoulders 22 which engage shoulder slots 26 depending into the frame 14 are, as with the mode of FIGS. 1-12, positioned to extend adjacent opposing sides of the lenses 12 in the assembly 18 which are shown both formed as a single shield lens 12. Any lens assembly 18 configured as shown in FIG. 14, with the shoulders positioned adjacent opposing sides of the lens 12, will form a removable engagement with a frame 14 and form the assembled device 10 of FIG. 13. In this removable engagement as with that of FIGS. 1-2, the first and second shoulders 22 engaged to positions at opposite sides of the lens 12, will slide into respective complimentary shaped post slots 28 depending into the body of the frame 14.

As can be seen in FIGS. 13-14, the shoulders 22 each have a curved surface depression defining a ball recess 30 which during engagement is engaged by a biased ball 36 in the same fashion as shown in FIG. 5. This provides for a smooth and easy sliding engagement of the shoulder 22 into respective complimentary shaped shoulder slots 26 formed into the body 15 of the frame 14, while still providing a firm mount and resistance to dislodgement of the lens assembly 18.

Additionally shown in FIG. 14 are a mount marker 42 positioned on one or both of the shoulders 22 which becomes viewable through aperture 44 which communicates with a shoulder slot 28. This mount marker 42 is viewable through the aperture 44 only when the shoulder 22 is fully and properly engaged within the respective shoulder slot 26 in the frame 14. The mount marker 44 is spaced from the center of the recess 30 such that if the shoulder 22 is not fully inserted to a point where the ball 36 engages with the ball recess 30, the mount marker 42 will not be visible through the aperture 44. Thus, the mount marker 42 provides a visually discernable confirmation of proper mounting of the lens assembly 18 into the frame 14 which is viewable by the user.

In FIG. 15 is shown a perspective view of the device 10 in the assembled mode of FIG. 13. A rear view of the device 10 of FIG. 13 is shown in FIG. 16 and a first side view of the device 10 of FIG. 13 is shown in FIG. 17.

Shown in FIG. 18 is a bottom side view of the device 10 of FIG. 13 the opposite side of which is shown in the top view of FIG. 19.

While all of the fundamental characteristics and features of the lens frame and interchangeable eyewear system herein have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that upon reading this disclosure and becoming aware of the disclosed novel and useful interchangeable eyewear system herein disclosed, that various substitutions, modifications, and variations may occur to and be made by those skilled in the art, without departing from the spirit or scope of the invention. Consequently, all such modifications and variations and substitutions, as would occur to those skilled in the art are considered included within the scope of the retracting leash invention herein as defined by the following claims.

What is claimed is:

1. An eyewear device comprising:
   a frame having a body extending between a first end of said frame and a second end thereof;
   a first temple rotationally engaged at said first end of said frame and a second temple rotationally engaged at a second end of said frame;
   a lens assembly having a first side opposite a second side and having two lens portions therebetween;
   a first shoulder engaged with said lens assembly to a position adjacent said first side of said lens assembly;
   a second shoulder engaged with said lens assembly to a position adjacent said second side of said lens assembly;
   at least one ball positioned within a ball cavity in said body of said frame;
   said ball biased to position a projecting portion of said ball within said first shoulder slot; and
   said projecting portion biasly locating into a first ball recess formed in said first shoulder while said lens assembly is in said removable engagement with said frame,
   said lens assembly positionable to a removable engagement with said frame having said first shoulder slidingly positioned within a first shoulder slot depending into said body of said frame and having said second shoulder slidingly positioned within a second shoulder slot depending into said body of said frame, and having edge portions of said two lens portions contacting against a central portion of said body of said frame in-between said first end of said frame and said second end of said frame.

2. The eyewear device of claim 1 additionally comprising:
   a second ball positioned within a second ball cavity in said body of said frame;
   said second ball biased to position a projecting portion of said second ball within said second shoulder slot; and
   said projecting portion of said second ball biasly locating into a second ball recess formed in said second shoulder while said lens assembly is in said removable engagement with said frame.

3. The eyewear device of claim 2 additionally comprising:
   said lens assembly having a connecting member engaged to first ends of said two lens portions;
   a post extending from said connecting member in between said two lens portions;
   a post slot depending into said body of said frame; and
   said post locating within said post slot with said lens assembly in said removable engagement with said frame.

4. The eyewear device of claim 3 additionally comprising:
   a window aperture communicating with said post slot from an exterior surface of said body of said frame; and
   an endwall of said post visible through said window aperture only with said lens assembly in said removable engagement with said frame.

5. The eyewear device of claim 3 additionally comprising:
   edge portions of said two lens portions contacting against a central portion of said body of said frame within a slot depending into said body of said frame.

6. The eyewear device of claim 4 additionally comprising:
   edge portions of said two lens portions contacting against a central portion of said body of said frame within a slot depending into said body of said frame.

7. The eyewear device of claim 2 wherein said two lens portions are formed in a shield.

8. The eyewear device of claim 1 additionally comprising:
   said lens assembly having a connecting member engaged to first ends of said two lens portions;
   a post extending from said connecting member in-between said two lens portions;
   a post slot depending into said body of said frame; and
   said post locating within said post slot with said lens assembly in said removable engagement with said frame.

9. The eyewear device of claim 8 additionally comprising:
   edge portions of said two lens portions contacting against a central portion of said body of said frame within a slot depending into said body of said frame.

10. The eyewear device of claim 1 wherein said two lens portions are formed in a shield.

11. The eyewear device of claim 10 additionally comprising:
    said first shoulder having a marker positioned thereon;
    an aperture communicating through said body of said frame to said first shoulder slot; and
    said marker visible through said aperture only with said lens assembly positioned in said removable engagement.

12. An eyewear device comprising:
    a frame having a body extending between a first end of said frame and a second end thereof;
    a first temple rotationally engaged at said first end of said frame and a second temple rotationally engaged at a second end of said frame;
    a lens assembly having a first side opposite a second side and having two lens portions therebetween;
    a first shoulder engaged with said lens assembly to a position adjacent said first side of said lens assembly;
    a second shoulder engaged with said lens assembly to a position adjacent said second side of said lens assembly;
    said lens assembly having a connecting member engaged to first ends of said two lens portions;
    a post extending from said connecting member in between said two lens portions;
    a post slot depending into said body of said frame; and
    said post locating within said post slot with said lens assembly in said removable engagement with said frame,
    said lens assembly positionable to a removable engagement with said frame having said first shoulder slidingly positioned within a first shoulder slot depending into said body of said frame and having said second shoulder slidingly positioned within a second shoulder slot depending into said body of said frame, and having edge portions of said two lens portions contacting against a central portion of said body of said frame in-between said first end of said frame and said second end of said frame.

13. The eyewear device of claim 12 additionally comprising:
a window aperture communicating with said post slot from an exterior surface of said body of said frame; and
an endwall of said post visible through said window aperture only with said lens assembly in said removable engagement with said frame.

14. The eyewear device of claim 13 additionally comprising:
edge portions of said two lens portions contacting against a central portion of said body of said frame within a slot depending into said body of said frame.

15. The eyewear device of claim 12 additionally comprising:
a window aperture communicating with said post slot from an exterior surface of said body of said frame; and
an endwall of said post visible through said window aperture only with said lens assembly in said removable engagement with said frame.

16. The eyewear device of claim 15 additionally comprising:
edge portions of said two lens portions contacting against a central portion of said body of said frame within a slot depending into said body of said frame.

17. The eyewear device of claim 12 additionally comprising:
edge portions of said two lens portions contacting against a central portion of said body of said frame within a slot depending into said body of said frame.

18. The eyewear device of claim 12 additionally comprising:
said first shoulder having a marker positioned thereon;
an aperture communicating through said body of said frame to said first shoulder slot; and
said marker visible through said aperture only with said lens assembly positioned in said removable engagement.

* * * * *